United States Patent
Amino et al.

(10) Patent No.: US 6,335,461 B1
(45) Date of Patent: Jan. 1, 2002

(54) PROCESS FOR PURIFICATION OF ASPARTAME DERIVATIVE

(75) Inventors: Yusuke Amino; Tadashi Takemoto, both of Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/515,097

(22) Filed: Feb. 29, 2000

(30) Foreign Application Priority Data

Oct. 23, 1997 (JP) ............................................. 9-290216
Oct. 21, 1998 (WO) ............................... PCT/JP98/04783

(51) Int. Cl.$^7$ ........................................... C07C 229/00
(52) U.S. Cl. .......................................... 560/41; 560/40
(58) Field of Search ...................... 560/40, 41

(56) References Cited

U.S. PATENT DOCUMENTS

| | | | | |
|---|---|---|---|---|
| 3,901,871 | A | * | 8/1975 | Anderson |
| 4,017,472 | A | * | 4/1977 | Farkas et al. |
| 4,440,667 | A | * | 4/1984 | Dryden et al. |
| 5,055,588 | A | * | 10/1991 | Takase et al. |
| 5,480,668 | A | | 1/1996 | Nofre et al. |
| 5,510,508 | A | * | 4/1996 | Claude et al. |
| 5,728,862 | A | | 3/1998 | Prakash |
| 5,968,581 | A | | 10/1999 | Nakamura et al. |

FOREIGN PATENT DOCUMENTS

| | | |
|---|---|---|
| JP | 8-506206 | 4/1996 |
| JP | 10-248520 | 9/1998 |
| JP | 10-248521 | 9/1998 |
| WO | WO 98/32767 | 7/1998 |

OTHER PUBLICATIONS

Ault, Addison. Techniques and Experiments for Organic Chemistry, Fifth Edition. Waveland Press Inc., pp 110–111, 1994.*

* cited by examiner

*Primary Examiner*—Paul J. Killos
*Assistant Examiner*—Mahreen Chaudhry
(74) *Attorney, Agent, or Firm*—Oblon, Spivak, McClelland, Maier & Neustadt, P.C.

(57) ABSTRACT

In the separation and purification of N-[N-(3,3-dimethylbutyl)-L-α-aspartyl]-L-phenylalanine methyl ester produced in the reductive alkylation of aspartame (APM) with 3,3-dimethylbutylaldehyde, the APM used in the starting material for the alkylation, which is difficult to be separated by recrystallization only from the crude crystals of the reaction product, can be separated and removed by extraction or solution thereof with the specified organic solvent from the concentrated reaction solution of the reductive alkylation or from the crude crystals of the product therefrom, and further N,N-di(3,3-dimethylbutyl)-APM as the by-product can be separated and removed by means for separation and purification, such as crystallization, chromatography, extraction, treatment with the activated charcoal, etc. As a result, N-[N-(3,3-dimethylbutyl)-L-α-aspartyl]-L-phenylalanine methyl ester which is a sweetener having a high degree of sweetness can be purified efficiently, and also the APM derivative in a high purity is possibly produced industrially.

6 Claims, No Drawings

PROCESS FOR PURIFICATION OF ASPARTAME DERIVATIVE

TECHNICAL FIELD OF INVENTION

The present invention relates to a process for purification of a sweetening substance of N-[N-(3,3-dimethylbutyl)-L-α-aspartyl]-L-phenylalanine methyl ester represented by the following formula (1), which may be abbreviated to "N-(3,3-dimethylbutyl)-APM" or "APM derivative", and to a process for production of high purity APM derivative.

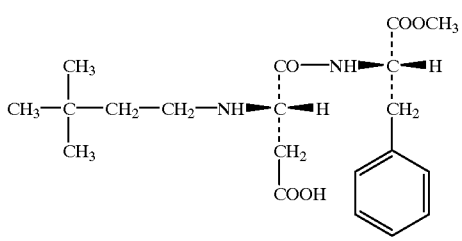

(1)

BACKGROUND OF ART

In recent years, as eating habits have been improved to a high level, fatness caused by excessive sugar intake and diseases accompanied by fatness have been at issue. Accordingly, the development of a low-calory sweetening agent (sweetener) that replaces sugar has been in demand. As a sweetening agent that has been widely used at present, there is aspartame (APM, represented by the following formula (2)) which is excellent in safety and quality of sweetness. However, this is somewhat problematic in stability.

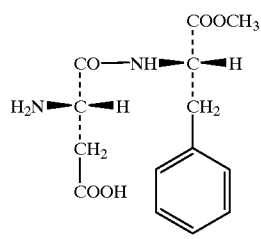

(2)

In the French Patent No.2697844 specification, it is stated that derivatives in which an alkyl group is introduced on an amino group of aspartic acid constituting the APM are studied and N-(3,3-dimethylbutyl)-APM represented by the above-mentioned formula (1) is markedly improved in the sweetening potency. For the production of N-(3,3-dimethylbutyl)-APM, a process for alkylating APM reductively in the presence of 3,3-dimethylbutylaldehyde with sodium cyano borohydride in methanol (refer to FR 2697844 specification), and a process for alkylating APM reductively in the presence of 3,3-dimethylbutylaldehyde with platinum carbon as the catalyst (refer to WO95/30689 specification) are known. And however, a reaction is carried out according to descriptions in such above patent specifications, 3,3-dimethylbutylaldehyde and APM both unreacted, or N,N-di(3,3-dimethylbutyl)-APM into which 2 alkyl groups have been introduced, represented by the following formula (3) are mixed in the reaction solution (mixture) and the crude crystals of the product, to no small extent.

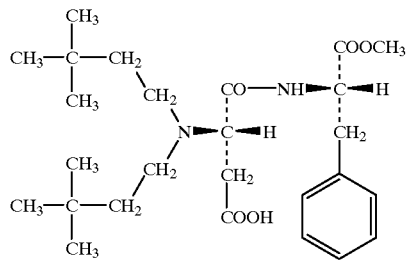

(3)

Of the compounds stated above, 3,3-dimethylbutylaldehyde is removed by dryness under reduced pressure or washing (washup) with comparative ease, because it has a low boiling point or is soluble in a bad solvent such as hexane. On the other hand, it is difficult to remove APM and N,N-di(3,3-dimethylbutyl)-APM by recrystallizing once or twice the residue from which the catalysts has been removed as described in the above-mentioned patent specifications, and accordingly it is not possible to obtain N-(3,3-dimethylbutyl)-APM having satisfactory purity. Particularly, when APM is remained therein, it is difficult to remove it by crystallization. Because 3,3-dimethylbutylaldehyde is problematic in odor (smell), in the reaction it is desirable to consume out the aldehyde as much as possible by using excess of APM. In such case, the APM (unreacted) is remained in the reaction solution, and therefore it is important to establish a method for removal thereof efficiently.

PROBLEM TO BE SOLVED BY INVENTION

The problem to be solved by the invention is to provide, in the reductive alkylation of aspartame (APM) with 3,3-dimethylbutylaldehyde to produce N-(3,3-dimethylbutyl)-APM, a process for an effective separation or removal of APM remained in the reaction solution or the crude crystals of the product, or N,N-di(3,3-dimethylbutyl)-APM produced as the by-product therein.

DISCLOSURE OF INVENTION

In order to solve the problem, the present inventors have studied earnestly a process to purify N-(3,3-dimethylbutyl)-APM, and found the fact that N-(3,3-dimethylbutyl)-APM can be easily purified utilizing differences in solubility between APM and N-(3,3-dimethylbutyl)-APM in various solvents, differences in crystallinity between N-(3,3-dimethylbutyl)-APM and N,N-di(3,3-dimethylbutyl)-APM in various crystallizing solvents and differences in affinity to the carriers used on chromatography. Based on the above findings, the present invention has been completed.

That is to say, the present invention is directed to, in a process for separation and purification of N-[N-(3,3-dimethylbutyl)-L-α-aspartyl]-L-phenylalanine methyl ester comprising the steps of alkylating reductively APM with 3,3-dimethylbutylaldehyde to produce the APM derivative represented by the above-mentioned formula (1), i.e., N-[N-(3,3-dimethylbutyl)-L-α-aspartyl]-L-phenylalanine methyl ester, and separating the APM derivative from the reaction solution for purification thereof, the improvement comprising the steps:

extracting said APM derivative with an organic solvent from said reaction solution concentrated or from crude crystals of the product obtained from said reaction solution; or washing said reaction solution concentrated or said crude crystals with an organic solvent, to dissolve said APM derivative therein, and thereby to separate and remove APM remained in said reaction solution at the time of completion of the reductive alkylation therefrom, and separating an impurity contained in the organic solvent, i.e., N,N-di(3,3-dimethylbutyl)-APM represented by the above-mentioned formula (3) to be removed by using at least one operation selected from the following operations, A–D:

Operation A: Operation for crystallization of said APM derivative to separate (weeding out) and remove N,N-di(3,3-dimethylbutyl)-APM dissolved in the mother liquor therefrom;

Operation B: Operation for separating and removing N,N-di(3,3-dimethylbutyl)-APM on chromatography therefrom;

Operation C: Operation for separating and removing N,N-di(3,3-dimethylbutyl)-APM therefrom on extraction therefor; and Operation D: Operation for separating and removing N,N-di(3,3-dimethylbutyl)-APM by adsorbing the same to the activated charcoal on treatment with activated charcoal.

In the present invention, the following contents are contained.

1. The above process, wherein the organic solvent used for solution of the APM derivative in the extraction of the desired product from the solution obtained by concentrating the reaction solution or the washup (washing) of the crude crystals of the product is one solvent or a mixed solvent of more than one solvents, selected from the group consisting of ethyl acetate, methyl acetate, toluene, hexane, tetrahydrofuran, acetonitrile, dimethoxyethane, ethyl ether, isopropyl alcohol, ethyl alcohol, methyl alcohol, dichloromethane (methylene chloride), chloroform, acetone and methyl ethyl ketone.

2. The above process, wherein the organic solvent used for crystallization of said APM derivative is one solvent or mixed solvent of more than one solvents, selected from the group consisting of ethyl acetate, methyl acetate, toluene, hexane, tetrahydrofuran, acetonitrile, dimethoxyethane, ethyl ether, isopropyl alcohol, ethyl alcohol, methyl alcohol, dichloromethane (methylene chloride), chloroform, acetone and methyl ethyl ketone, or a mixed solvent of water and at least one solvent selected from the group consisting of tetrahydrofuran, acetonitrile, isopropyl alcohol, ethyl alcohol, methyl alcohol, acetone and methyl ethyl ketone.

3. The above process, wherein the chromatography is at least one of column chromatography having silica gel for a carrier, and column chromatography having activated charcoal for a carrier.

4. In a process for production of N-[N-(3,3-dimethylbutyl)-L-α-aspartyl]-L-phenylalanine methyl ester or production of N-[N-(3,3-dimethylbutyl)-L-α-aspartyl]-L-phenylalanine methyl ester and N,N-di(3,3-dimethylbutyl)-APM comprising the step of separating N-[N-(3,3-dimethylbutyl)-L-α-aspartyl]-L-phenylalanine methyl ester and N,N-di(3,3-dimethylbutyl)-APM each other from a mixture containing at least said two compounds, the improvement comprising the step of:

subjecting said mixture to at least one operation selected from the following operations: A–D:

Operation A: Operation for crystallization of said APM derivative to separate (weeding out) and remove N,N-di(3,3-dimethylbutyl)-APM dissolved in the mother liquor therefrom;

Operation B: Operation for separating and removing N,N-di(3,3-dimethylbutyl)-APM on chromatography therefrom;

Operation C: Operation for separating and removing N,N-di(3,3-dimethylbutyl)-APM therefrom on extraction therefor; and Operation D: Operation for separating and removing N,N-di(3,3-dimethylbutyl)-APM by adsorbing the same to the activated charcoal on treatment with activated charcoal.

As for the starting materials in the process, in addition to a mixture of the above 2 compounds only, for examples, the reaction mixture from the above reductive alkylation, roughly purified material obtained after removal of unreacted APM as the starting material, and the like are enumerated. Therefore, a separating method thereof through any one of the above operations: A–D, which is carried out during the process for separating and producing any one compound of the above 2 compounds in the pure form, from a mixture comprising at least the above-mentioned 2 compounds, is covered by the process (improvement) in the present invention.

5. The APM derivative produced in any one process of the above processes in the present invention.

6. A sweetener comprising APM derivative, which may contain at least one carrier appropriate for sweeteners (sweetening agents), if necessary, or a method for giving or imparting sweetness comprising the step of using or adding the derivative for a material requesting sweetness, such as foods requesting sweetness.

EMBODIMENTS OF INVENTION

In the process for reaction of reductive alkylation of the APM or a derivative of APM having a protecting group which can be easily removed, such as N-benzyloxycarbonyl-β-O-benzyl-α-L-aspartyl-L-phenylalanine methyl ester, β-O-benzyl-α-L-aspartyl-L-phenylalanine methyl ester, to produce N-(3,3-dimethylbutyl)-APM, the solution of N-(3,3-dimethylbutyl)-APM containing little APM can be obtained by extracting or washing the material obtained by concentrating the reaction solution or crude crystals of the product (APM derivative) therefrom with an organic solvent which can dissolve N-(3,3-dimethylbutyl)-APM, since the APM remained in the reaction solution or the crude crystals of the APM derivative is almost difficult to be dissolved in most of organic solvents.

When the reaction solution is concentrated to precipitate the crystals, thus concentrated solution containing the crystals precipitated may be subjected to an extraction operation with an organic solvent, or a concentrated solution obtained after separating the crystals (crude) thereof may be subjected to an extraction operation with an organic solvent, while thus separated and obtained crude crystals may be dissolved in an organic solvent or washed with an organic solvent, separately.

For the organic solvent(s) used in extracting the desired compound, or washing the crude crystals to dissolve the desired compound, one solvent or a mixed solvent of more than one solvents, selected from the group consisting of ethyl acetate, methyl acetate, toluene, hexane, tetrahydrofuran, acetonitrile, dimethoxyethane, ethyl ether, isopropyl alcohol, ethyl alcohol, methyl alcohol, dichloromethane (methylene chloride), chloroform, acetone and methyl ethyl ketone can be employed. And further, in order to remove the APM as much as possible, an organic solvent which is not much (hardly) mixed with water homogeneously, such as ethyl acetate, methyl acetate, toluene, dimethoxyetane, dichloromethane and chloroform are preferably employed. In order to remove much more completely the APM, it is efficient to wash the organic layer obtained in the extraction with such organic solvent, with water or aqueous solution which is in the neutral, weak acidic or weak alkaline state.

Thus obtained organic layer is dried with a drying agent such as anhydrous magnesium sulfate, or is dehydrated in the azeotropic distillation to remove water as much as possible, and thereafter concentrated. From thus obtained residue, N-(3,3-dimethylbutyl)-APM is crystallized with one solvent or a mixed solvent of more than one solvents, selected from the group consisting of ethyl acetate, methyl acetate, toluene, hexane, tetrahydrofuran, acetonitrile, dimethoxyethane, ethyl ether, isopropyl alcohol, ethyl alcohol, methyl alcohol, dichloromethane, chloroform, acetone and methyl ethyl ketone to separate or remove N,N-di(3,3-dimethylbutyl)-APM dissolved in the mother liquor, because the N,N-di(3,3-dimethylbutyl)-APM is an oily viscous material poor in crystallinity (crystallizing properties).

For another convenient crystallization method, the following process is possible.

The organic layer obtained in the extraction from the reaction solution, particularly concentrated solution therefrom or washing the crude crystals of the product may be directly concentrated to remove the organic solvent involved therein, and the solvent may be replaced by a solvent which can mix with water homogeneously, such as tetrahydrofuran, acetonitrile, isopropyl alcohol, ethyl alcohol, methyl alcohol, acetone and methyl ethyl ketone, or a mixed solvent obtained from one or more solvents selected from the group of such solvents, and further water may be added thereto. Thus obtained solution may possibly concentrated to precipitate N-(3,3-dimethylbutyl)-APM in the crystalline form.

In case that a crystallization is carried out using a mixed solvent of water and methanol as the crystallization solvent therefor, N,N-di(3,3-dimethylbutyl)-APM is separated or removed by being dissolved in the mother liquor when a ratio of methanol thereto is sufficiently high, because it is not easily crystallized although a solubility of N,N-di(3,3-dimethylbutyl)-APM is lower than that of N-(3,3-dimethylbutyl)-APM in such mixed solvent.

In order to promote crystallization of N-(3,3-dimethylbutyl)-APM, it is effective to adjust the pH value of the solution to the neighborhood of its isoelectric point or to add seed crystals thereof thereto.

For the method to separate or remove N,N-di(3,3-dimethylbutyl)-APM, a separation method through chromatography is also effective. For example, the residue is put on the silica gel, an elution is carried out using an ethyl acetate, a mixed solvent of ethyl acetate and chloroform, a mixed solvent of ethyl acetate and methanol, or a mixed solvent of ethyl acetate, chloroform and methanol as an eluent (eluting solution) to separate easily N-(3,3-dimethylbutyl)-APM and N,N-di(3,3-dimethylbutyl)-APM from each other.

For the more convenient method to remove N,N-di(3,3-dimethylbutyl)-APM, it is also effective to subject the solution of N-(3,3-dimethylbutyl)-APM to an extraction operation, followed by a washup (washing) operation with a solvent which does not mix with water homogeneously. For example, N-(3,3-dimethylbutyl)-APM is dissolved in a mixed solvent of water and methanol, and the solution is subjected to an extraction operation with a mixed solvent of ethyl acetate and ethyl ether, ethyl acetate and hexane, or the like to separate and remove N,N-di(3,3-dimethylbutyl)-APM.

A method to remove N,N-di(3,3-dimethylbutyl)-APM by adsorbing it to the activated charcoal, is also effective. In the treatment using the activated charcoal, it may be operated in a batch process or in a process for placing the residue on the activated charcoal filled in the column and then eluting N-(3,3-dimethylbutyl)-APM with methanol or a mixed solvent of methanol and water.

In case that the APM derivative separated for purification or produced in the present invention may be used for a sweetener or used for a production thereof, there is no difficulties, and known methods in the producing methods of the sweetening agents (sweeteners) or the using methods of the sweetening agents may be applied or utilized easily in the present invention.

PREFERRED EMBODIMENTS

The present invention is illustrated specifically by referring to the following Examples.

EXAMPLE 1

According to the descriptions in the FR Pat. No. 2697844 specification, 10.6 g of APM (aspartame), 5 ml of 3,3-dimethylbutylaldehyde and 1.6 g of sodium cyano borohydride were reacted in methanol and the resulting solution was concentrated under reduced pressure. To the mixture, water was added, and it was neutralized with the addition of 1N-HCl aqueous solution to precipitate an oily material. The material was extracted twice with 100 ml of ethyl acetate. Thus obtained organic layer was washed twice with 50 ml of water, and then washed once with 50 ml of a saturated aqueous solution of sodium chloride, and then dried over anhydrous magnesium sulfate. Then, the magnesium sulfate was removed by filtration, and the filtrate was concentrated. The resulting material was analyzed by the thin layer chromatography (TLC), and thereby it was found that APM was not contained therein. And however, N-(3,3-dimethylbutyl)-APM, N,N-di(3,3-dimethylbutyl)-APM and an unknown compound having a low polarity, were detected. The residue was put on the column filled with 170 ml of silica gel and eluted with an eluting solution of ethyl acetate and chloroform at a ratio of 3:1, and an eluting solution of ethyl acetate, chloroform and methanol at a ratio of 3:1:1 to obtain N-(3,3-dimethylbutyl)-APM as a viscous oily material. A mixed solvent (20 ml) of water and methanol was added thereto, and the resulting mixture was continuously concentrated to obtain crystals. Thus obtained crystals were collected by filtration and dried to obtain 2.58 g of N-(3,3-dimethylbutyl)-APM.

EXAMPLE 2

According to the descriptions in the WO 95/30689 specification, 67.4 g of APM, 25 ml of 3,3-dimethylbutylaldehyde and 15 g of 5% palladium-carbon in a mixed solvent of methanol-0.1M acetic acid aqueous solution were reacted for three hours in a hydrogen stream. The catalyst was removed by filtration, and the catalyst was washed sufficiently with methanol. The filtrate and the methanol used in the washing step were combined together, and thus obtained solution was concentrated to adjust to about one third (⅓) of the solution in volume, and then 100 ml of water added thereto. Thus obtained mixture was concentrated further to precipitate crystals. The crystals were collected by filtration and analyzed by TLC. As a result, APM and N-(3,3-dimethylbutyl)-APM were detected, and however little (scarcely) N,N-di(3,3-dimethylbutyl)-APM was detected. On the other hand, in the mother liquor, which is thereafter referred to as "Mother Liquor 1", APM, N-(3,3-dimethylbutyl)-APM and N,N-di(3,3-dimethylbutyl)-APM were detected.

To thus obtained crystals, 200 ml of ethyl acetate and a small amount of water were added, and then the mixture was stirred for 30 minutes and then subjected to the filtration. To thus obtained insoluble material, 200 ml of ethyl acetate was further added and the mixture was stirred for 30 minutes, and then subjected again to the filtration. Two filtrates were combined together and the solution was allowed to be separated into 2 layers therein. The organic layer was washed with 100 ml of water, and concentrated under reduced pressure. Here, TLC analysis was carried out and revealed that almost all the APM was separated and removed therefrom. The operation for adding methanol (50 ml) thereto and concentrating the solution under reduced pressure, was repeated three times, and then, the operation for adding water (50 ml) thereto and concentrating the solution under reduced pressure was repeated 3 times to precipitate crystals in part. Thus obtained solution was stored in the refrigerator over one night. Thus produced crystals were collected by filtration and washed with a small amount of water, and dried to obtain 36.8 g of N-(3,3-dimethylbutyl)-APM having a purity of 99.5% on the analysis with HPLC (High Performance Liquid Chromatography).

EXAMPLE 3

The Mother Liquor 1 obtained in the above-mentioned Example 2, was adjusted to pH 5 with the addition of 1N-NaOH aqueous solution and concentrated to about 100 ml of the solution. This mixture was extracted twice with 100 ml of ethyl acetate, and then the organic layer was washed with 50 ml of water. The organic layer was analyzed by TLC, and as a result, it contained little APM. In the same manner as in the Example 2, the solvent was replaced by a mixed solvent of water and methanol, and the solution was further concentrated to precipitate an oily material. The oily material was analyzed by TLC, and as a result, it was N,N-di(3,3-dimethylbutyl)-APM. The solution was washed twice with 50 ml of a mixed solution of ethyl acetate and ethyl ether in the ratio of 1:3, and concentrated continuously to precipitate crystals. The crystals were collected by filtration to obtain 4.0 g of N-(3,3-dimethylbutyl)-APM. The crystals were analyzed, and as a result little N,N-di(3,3-dimethylbutyl)-APM was contained therein.

EXAMPLE 4

The solvent of Mother Liquor 1 obtained in the same manner as in the Example 2, was replaced by a mixed solvent of water and methanol in the same operation as that in the Example 3. When a small amount of oily material was precipitated, 5 g of the activated charcoal were added thereto, and the mixture was stirred for some time. The activated charcoal was removed by filtration, and the filtrate was concentrated. The precipitated crystals were collected by filtration and dried to obtain 2.5 g of N-(3,3-dimethylbutyl)-APM. The crystals were analyzed, and as a result, N,N-di(3,3-dimethylbutyl)-APM was not contained therein.

EFFECTS OF INVENTION

In the present invention, when N-(3,3-dimethylbutyl)-APM is produced in the reaction for reductive alkylation of APM with 3,3-dimethylbutylaldehyde, APM unreacted, or N,N-di(3,3-dimethylbutyl)-APM as the by-product, respectively remained in the reaction solution or the crude crystals of the product obtained can be efficiently separated and removed.

What is claimed is:

1. A method of purifying N-[N-3,3-dimethylbutyl)-L-α-aspartyl]-L-phenylalanine methyl ester, comprising extracting said N-[N-3,3-dimethylbutyl)-L-α-aspartyl]-L-phenylalanine methyl ester and N,N-di(3,3-dimethylbutyl)-APM from an aqueous solution comprising the N-[N-3,3-dimethylbutyl)-L-α-aspartyl]-L-phenylalanine methyl ester, APM, and N,N-di (3,3-dimethylbutyl)-APM with an organic solvent, wherein the aqueous solution may be a slurry, wherein said organic solvent is selected from the group consisting of ethyl acetate, methyl acetate, toluene, tetrahydrofuran, acetonitrile, dimethoxyethane, isopropyl alcohol, ethyl alcohol, methyl alcohol, chloroform, acetone, methyl ethyl ketone, and mixtures thereof and further purifying the N-[N-3,3-dimethylbutyl)-L-α-aspartyl]-L-phenylalanine methyl ester by a method selected from the group consisting of:

(A) crystallizing said N-[N-3,3-dimethylbutyl)-L-α-aspartyl]-L-phenylalanine methyl ester;
   (B) subjecting said N-[N-3,3-dimethylbutyl)-L-α-aspartyl]-L-phenylalanine methyl ester to chromatography;
   (C) extracting said N,N-di(3,3-dimethyl)-APM and
   (D) absorbing said N-[N-3,3-dimethylbutyl)-L-α-aspartyl]-L-phenylalanine methyl ester on activated charcoal.

2. The method of claim 1, wherein said organic solvent is ethyl acetate.

3. The method of claim 1, wherein in (A) said crystallizing comprises adding at least one organic solvent selected from the group consisting of ethyl acetate, methyl acetate, toluene, hexane, tetrahydrofuran, acetonitrile, dimethoxyethane, ethyl ester, isopropyl alcohol, ethyl alcohol, methyl alcohol, dichloromethane, chloroform, acetone, methyl ethyl ketone, and mixtures thereof.

4. The method of claim 1, wherein in (A) said crystallizing comprises adding a mixture of water and at least one organic solvent selected from the group consisting of tetrahydrofuran, acetonitrile, isopropyl alcohol, ethyl alcohol, methyl alcohol, acetone, and methyl ethyl ketone.

5. The method of claim 1, wherein in (B) said chromatography comprises silica gel or activated charcoal.

6. The method of claim 1, wherein in (C) said N,N-di(3,3-dimethylbutyl)-APM is extracted with an organic mixture selected from the group consisting of alkyl acetate/ether, ethyl acetate/diethyl ether, alkyl acetate/hydrocarbon, and ethyl acetate/hexane.

* * * * *

UNITED STATES PATENT AND TRADEMARK OFFICE
CERTIFICATE OF CORRECTION

PATENT NO. : 6,335,461 B1  Page 1 of 1
DATED : January 1, 2002
INVENTOR(S) : Amino et al.

It is certified that error appears in the above-identified patent and that said Letters Patent is hereby corrected as shown below:

<u>Title page,</u>
Item [62], Related U.S. Application information should read:

-- Related U.S. Application Data
[62] This application is a Continuation of PCT/JP98/04783, filed on Oct. 21, 1998. --

Item [30], Foreign Application Priority infrmation should read:
-- [30]   Foreign Application Priority Data
            Oct. 23, 1997  (JP) ....................... 9-290216 --

Signed and Sealed this

Twenty-sixth Day of November, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

PATENT NO. : 6,335,461 B1
DATED : January 1, 2002
INVENTOR(S) : Amino et al.

It is certified that error appears in the above-identified patent and that said Letters Patent is hereby corrected as shown below:

Title page,
Item [62], Related U.S. Application information should read
  -- Related U.S. Application Data
[62] This application is a Continuation of PCT/JP98/04783, filed on Oct. 21, 1998 --

Item [30], Foreign Application Priority information should read:
  -- [30] Foreign Application Priority Data
        Oct. 23, 1997 (JP) ………………....9-290216 --

This certificate supersedes Certificate of Correction issued November 26, 2002.

Signed and Sealed this

Twenty-ninth Day of June, 2004

JON W. DUDAS
*Acting Director of the United States Patent and Trademark Office*